United States Patent [19]
Katsurada

[11] Patent Number: 5,343,854
[45] Date of Patent: Sep. 6, 1994

[54] DEVICE FOR ESTABLISHING COMMUNICATION BETWEEN THE INTERIOR AND EXTERIOR OF ENDOSCOPE

[75] Inventor: Hiroyuki Katsurada, Tokyo, Japan
[73] Assignee: Asahi Kogaku Kogyo Kabushiki Kaisha, Tokyo, Japan
[21] Appl. No.: 52,672
[22] Filed: Apr. 27, 1993

[30] Foreign Application Priority Data

Apr. 28, 1992 [JP] Japan .................................. 4-108269

[51] Int. Cl.⁵ .............................................. A61B 1/00
[52] U.S. Cl. ............................................... 128/4
[58] Field of Search .................. 251/149.6; 128/4 A, 128/4, 6; 604/33, 249

[56] References Cited
U.S. PATENT DOCUMENTS 4,527,551 7/1985 Ishii .
4,878,484 11/1989 Miyagi ................................... 128/4

FOREIGN PATENT DOCUMENTS 59-19105 2/1984 Japan .
112802 4/1989 Japan .

*Primary Examiner*—Robert Bahr
*Assistant Examiner*—Beverly A. Meindl
*Attorney, Agent, or Firm*—Sughrue, Mion, Zinn, Macpeak & Seas

[57] ABSTRACT

A device that establishes communication between the interior and exterior of an endoscope using a communicating valve, and which is hygienic and free from leakage. The device has a valve opening member for causing a valve body to be disengaged from a valve seat against the urging force of biasing members, and has porous members which are permeable to air but impermeable to water, and which block the channels of communication between the interior and exterior of an endoscope. The device is detachable from the outside of the communicating valve.

7 Claims, 2 Drawing Sheets

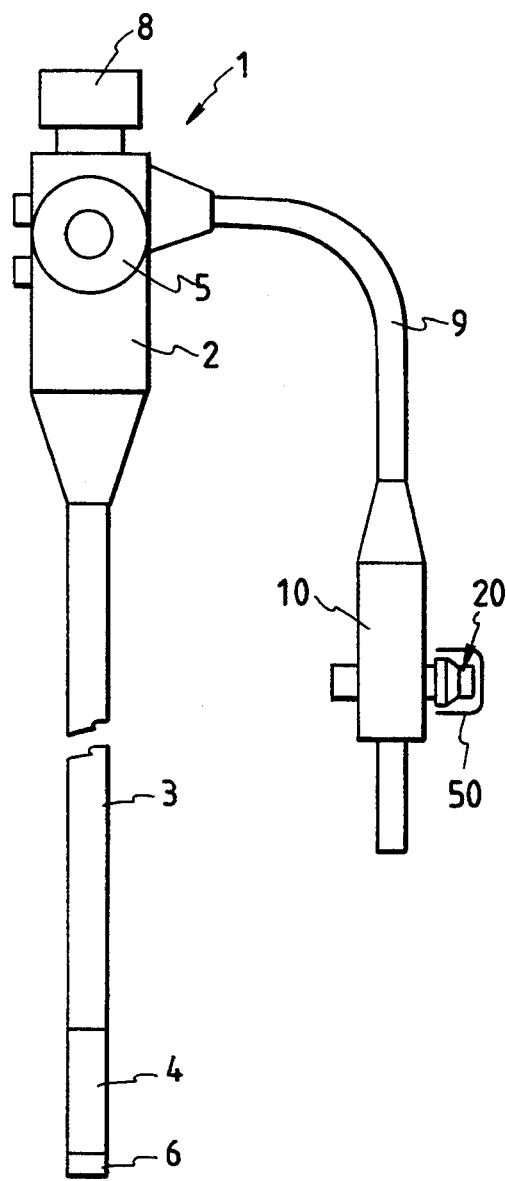
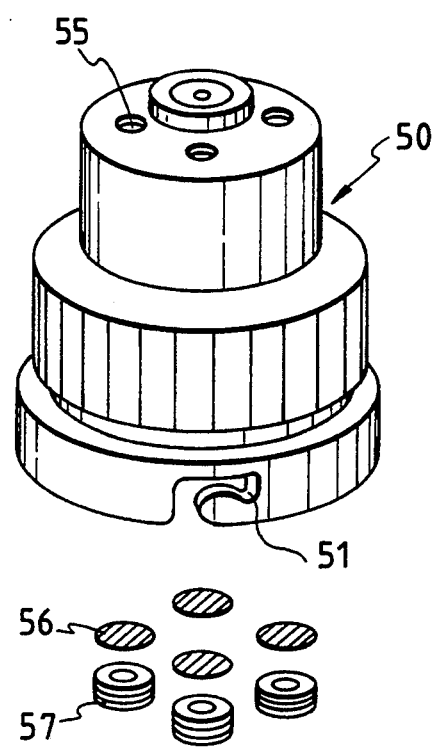

DEVICE FOR ESTABLISHING COMMUNICATION BETWEEN THE INTERIOR AND EXTERIOR OF ENDOSCOPE

The presented disclosure relates to subject matter contained in Japanese Application No. Hei-4-108269 filed Apr. 28, 1992, which is expressly incorporated herein by reference in its entirety.

BACKGROUND OF THE INVENTION

1. Field Of The Invention

The present invention relates to a device for establishing communication between the interior and exterior of an airtight endoscope.

2. Description Of The Related Art

Two known devices for establishing communication between the interior and exterior of an endoscope are described in Japanese Utility Model Publication HEI No. 1-12802 and Japanese Utility Model Laid-Open Publication SHO No. 59-19105. The device disclosed in the first publication has a communicating valve provided in the outer wall portion of an endoscope in such a way that a valve body is normally pressed against a valve seat by a biasing device to isolate the interior of the endoscope from its exterior. When the valve body is disengaged from the valve seat against the urging force of the biasing device, communication is established between the interior and exterior of the endoscope. The device disclosed in the second publication has an air permeable but water impermeable porous member provided in the interior of an endoscope in such a way that it blocks the channel of communication between the interior and exterior of the endoscope.

These devices, however, have limitations. The first device, which has the communicating valve, tends to become unhygienic since fluids getting into the valve cannot easily be purged. The second device, which has the porous member provided in the interior of the endoscope, is unreliable because the operator is unable to check for the breakage of the porous member and, therefore, its deterioration will progress unnoticed until water gets into the endoscope when it is washed.

SUMMARY OF THE INVENTION

An object of the invention is to provide a device that establishes communication between the interior and exterior of an endoscope using a communication valve and which eliminates hygiene and leakage problems.

This object is attained by a device for establishing communication between the interior and exterior of an endoscope, in which a communicating adapter is detachably provided on the outside of a communicating valve. The communicating valve is provided in the outer wall portion of the endoscope and a body thereof is normally pressed against a valve seat by a biasing device to isolate the interior of the endoscope from its exterior. When the valve body is disengaged from the valve seat against the urging force of the biasing device, communication is established between the interior and exterior of the endoscope. The communicating adapter includes a valve opening member for causing the valve body to be disengaged from the valve seat against the urging force of the biasing device and porous members that are permeable to air but impermeable to water and which block the channels of communication between the interior and exterior of the endoscope.

BRIEF DESCRIPTION OF THE DRAWINGS

FIG. 2 is a diagrammatic view showing the general composition of an endoscope fitted with the communicating device shown in FIG. 1;

FIG. 4 is a perspective view showing the communicating adapter used in the device shown in FIG. 1 in a disassembled state.

DETAILED DESCRIPTION OF THE PREFERRED EMBODIMENT

Figure 1:
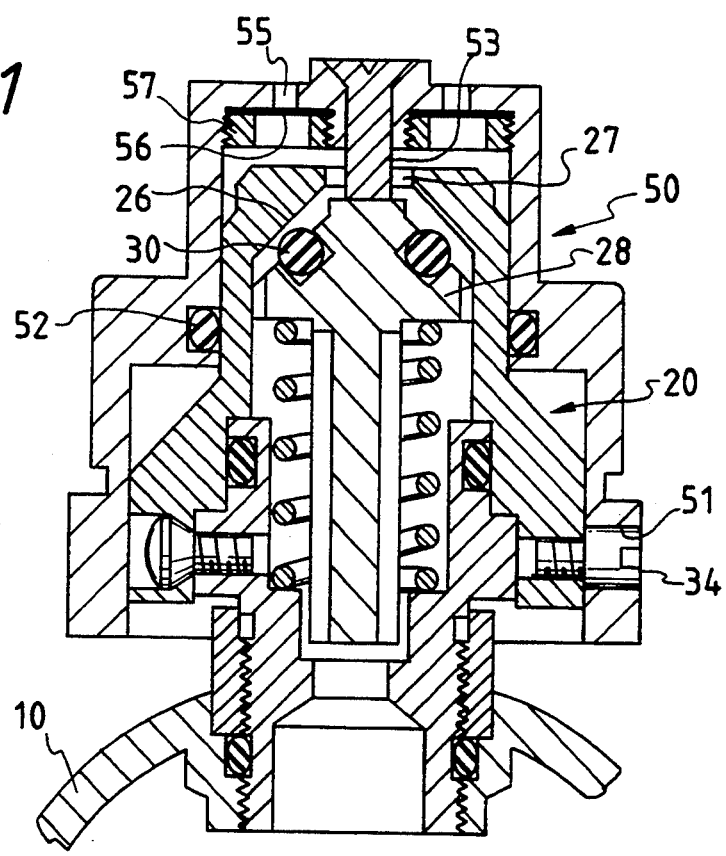
FIG. 1 is a longitudinal sectional view of a communicating device according to a preferred embodiment of the present invention.

The general setup of an endoscope according to a preferred embodiment of the present invention is shown in FIG. 2, in which the endoscope 1 includes a manipulating portion 2, and an inserting portion 3 made of a flexible tube. Formed at the distal end of the inserting portion 3 is a curving portion 4 that is freely bendable and can be remotely controlled with the manipulating portion 2. A curving control knob 5 is provided on the manipulating portion 2 to allow the operator to control the curving portion 4 in a known manner.

To permit bending with a small radius of curvature, the curving portion 4 is covered with a flexible rubber tube. The distal end of the curving portion 4 is connected to a sensor body 6 which incorporates objective optics and other necessary components. The manipulating portion 2 also has a projecting eyepiece unit 8 and is connected to a lightguide flexible tube 9 having a lightguide connector 10 provided at the distal end thereof which is to be connected to a light source unit (not shown).

Sealing, O-rings and other suitable devices are employed to ensure airtightness in all partition walls of the endoscope 1 that would otherwise communicate with the ambient atmosphere, and the interior of the endoscope is communicative throughout, from the curving portion 4 to the lightguide connector 10.

The lightguide connector 10 is fitted with a communicating valve 20 in such a way that communication between the interior and exterior of the endoscope 1 can be freely established or eliminated. A communicating adapter 50 is detachably mounted on the communicating valve 20.

Figure 3:
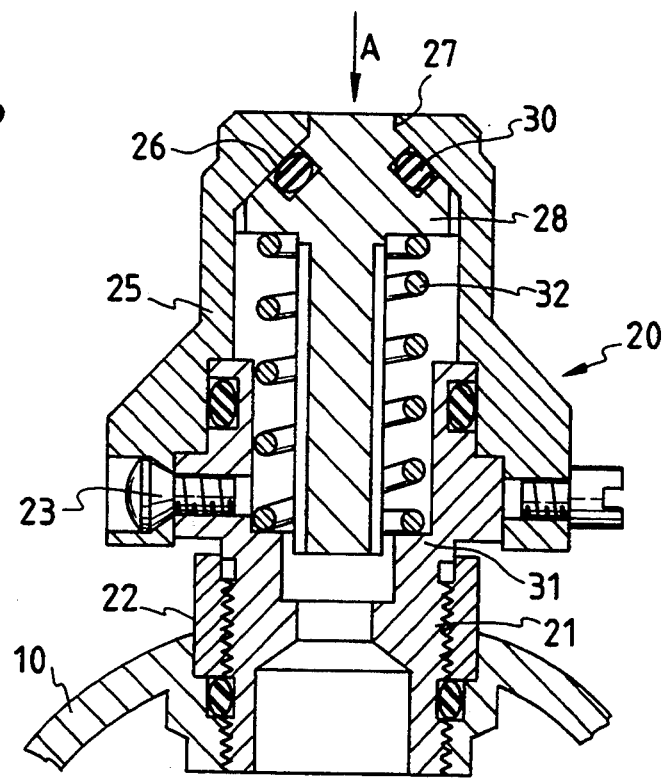
FIG. 3 is a longitudinal sectional view of the communicating valve used in the device shown in FIG. 1.

FIG. 3 is a longitudinal section of the communicating valve 20. A tubular member 21 is securely threaded into a tapped hole in the outer wall of the lightguide connector 10. A fixing nut 22 is then tightened on tubular member 21. A cap member 25 is secured to the tubular member 21 with a fixing screw 23. A tapered valve seat 26 is formed on the inner surface of the cap member 25. A hole 27, through which an airtightness removing member 53 is to be inserted, is formed in cap member 25, in the center of the valve seat 26.

A valve body 28 is inserted into the tubular member 21 in such a way it is movable in the axial direction thereof (up and down in FIG. 3). The valve body 28 has a bevelled surface that faces the valve seat 26, and a seal ring 30 is fitted in an annular groove formed in the bevelled surface.

A coiled compression spring 32 is fitted between a spring seat 31, formed on the inner surface of the tubular member 21, and the surface of the valve body 28 reverse to the bevelled surface so as to urge the valve body 28 in a direction away from the tubular member 21. The urging force of the coiled compression spring 32 causes the seal ring 30 on the valve body 28 to be normally pressed into contact with the valve seat 26, thereby isolating the interior of the endoscope from its exterior. If the operator pushes the valve body 27 inward in the direction of arrow A, against the urging force of the spring 32, the seal ring 30 of the valve body 28 will be moved away from the valve seat 26, whereby communication is established between the interior and exterior of the endoscope.

FIG. 1 is a longitudinal section of a communicating adapter 50 as it is mounted on the communicating valve 20, and FIG. 4 is a perspective view of the adapter 50 as it is disassembled into constituent parts. The communicating adapter 50 can be mounted in such a way that it is fitted over the communicating valve 20 and a hook-shaped groove 51 is engaged with a pin 34 projecting from the side wall of the lower part of the valve 20. (see FIGS. 1 and 4).

A circumferential groove is formed in the inner surface of the side wall of the adapter 50, and an O-ring 52 is fitted in that groove for sealing a gap defined between the inner surface of the adapter 50 and the outer surface of the communicating valve 20. An airtightness removing pin 53 is provided in the center of the top surface of the adapter 50 in such a way that it projects inwardly. The pin 53 passes through the hole 27 in the valve 20 so as to depress the valve body 28.

The pin 53 is fixed to the adapter 50, with an adhesive, such as epoxy resin, so that the pin 53 is securely bonded to the adapter 50. In the alternative, the pin 53 can be integrally formed with the adapter 50. As a result, the adapter 50 is maintained in an airtight condition in the area where the pin 53 is provided. A plurality of communicating holes 55 are formed in the top end face of the adapter 50. A porous membrane 56 is provided inside each hole 55 to close the holes 55 from the inside. The porous membranes 56 are formed of an air permeable but water impermeable material, such as a fluorine resin, and are securely pressed under each hole 55 by means of annular clamp nuts 57, with a sealant, such as a silicone-based sealant, being applied to the threaded portion of each clamp nut 57.

Hence, if the adapter 50 is fitted over the valve 20, the pin 34 is brought into engagement with the groove 51 and the pin 53 depresses the valve body 28, whereupon the seal ring 30 is disengaged from the valve seat 26 to keep the valve 20 in an open position. However, the communicating holes 55 are closed with the porous membranes 56 and, hence, air is permitted to flow from the interior of the lightguide connector 10, or the interior of the endoscope, to its exterior, or vice versa, but water is not. Accordingly, water is prevented from getting into the endoscope by means of the porous membranes 56 inside the communicating holes 55, and the blocked water can be readily rinsed off the porous membranes 56 by external cleaning.

In addition, the integrity of the porous membranes 56 can be visually checked from the outside and so deterioration of the porous membranes 56 can be easily detected. The operator may remove the communicating adapter 50 from the communicating valve 20 and, as shown in FIG. 4, the clamp nut 57 beneath the deteriorated membrane 56 is loosened and the deteriorated membrane 56 can be replaced. The same procedure may apply when one or more of the porous membranes 56 are removed for cleaning and disinfection.

The device of the present invention for establishing communication between the interior and exterior of an endoscope is such that porous members that are permeable to air but impermeable to water are provided on a communicating adapter which maintains an open state of a communicating valve. Therefore, dirty water coming from the outside is trapped by the porous members and can be readily washed off to keep the porous members clean. In addition, the porous members can be readily checked for any deterioration that may have occurred and thus water leakage is prevented.

Although the invention has been described herein with reference to specific embodiments, many modifications and variations therein will readily occur to those skilled in the art. Accordingly, all such variations and modifications are included within the intended scope of the invention.

What is claimed is:

1. A device for establishing communication between the interior and the exterior of an endoscope, in which a communicating adapter is detachably mounted on the outside of a communicating valve of the endoscope, the communicating valve being provided on an outer wall portion of the endoscope and having a valve body which is biased toward a valve seat by a biasing member so as to isolate the interior of the endoscope from the exterior of the endoscope, the communicating valve defining communication channels, which extend between the interior of the endoscope and the exterior of the endoscope, when the valve body is moved away from the valve seat, said device comprising:

a valve opening member extending from an interior surface of said communicating adapter and pressing said valve body against a force of said biasing member, when said communicating adapter is mounted on the communicating valve, to move said valve body away from said valve seat;

at least one porous member positioned on said communicating adapter so as to block said communication channels when said communicating adapter is mounted on the communicating valve, said porous members being permeable to air but not permeable to water.

2. A device as claimed in claim 1 further comprising:

a sealing member disposed on an inside surface of said communicating adapter, said sealing member being pressed against an outer surface of the communicating valve when said communicating adapter is mounted on said communicating valve.

3. A device as claimed in claim 2 wherein said communicating adapter and said communicating valve define a chamber therebetween which communicates with said communication channels, each of said porous members being mounted over an aperture formed in a wall of said communication adapter which defines said chamber so that said each porous member is visible through said aperture when said communicating adapter is mounted on said connecting valve.

4. A device as claimed in claim 3, said communicating adapter having threaded portions formed around each of said apertures, said communicating adapter further comprising a nut threadably engaged with each threaded portion, said porous members being held against said wall of said communication adapter by said nuts.

5. A device as claimed in claim 1, further comprising:

means for removably attaching said communicating adapter to an outside of the communicating valve.

6. A device as claimed in claim 5 wherein said attaching means comprises an open ended groove formed in said communicating adapter and a projection disposed on the communicating valve.

7. A device for establishing communication between the interior and the exterior of an endoscope, in which a communicating adapter is detachably mounted on the outside of a communicating valve of the endoscope, the communicating valve being detachably provided on an outer wall portion of the endoscope and having a valve body to isolate the interior of the endoscope from the exterior of the endoscope, the communicating valve defining communication channels, which extend between the interior of the endoscope and the exterior of the endoscope, when the valve body is moved, said device comprising:

means for sealing between said communicating valve and said communicating adapter when said communicating adapter is mounted on said communicating valve; and at least one porous member positioned on said communicating adapter so as to block a communication hole provided in the communicating adapter, said porous member being permeable to air but not permeable to water, and being visible through said communication hole.

* * * * *